(12) United States Patent
Sen et al.

(10) Patent No.: US 8,440,870 B2
(45) Date of Patent: May 14, 2013

(54) ONE-STEP CATALYTIC CONVERSION OF BIOMASS-DERIVED CARBOHYDRATES TO LIQUID FUELS

(75) Inventors: Ayusman Sen, State College, PA (US); Weiran Yang, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 721 days.

(21) Appl. No.: 12/455,816

(22) Filed: Jun. 5, 2009

(65) Prior Publication Data

US 2010/0307050 A1 Dec. 9, 2010

(51) Int. Cl.
*C10L 5/00* (2006.01)
*C07D 307/00* (2006.01)

(52) U.S. Cl.
USPC ............................................ 585/14; 549/429

(58) Field of Classification Search ............ 585/14; 549/429
See application file for complete search history.

(56) References Cited

U.S. PATENT DOCUMENTS

| | | | |
|---|---|---|---|
| 4,025,356 | A | 5/1977 | Nyman |
| 4,664,717 | A | 5/1987 | Young |
| 5,536,325 | A | 7/1996 | Brink |
| 6,423,145 | B1 | 7/2002 | Nguyen |
| 2003/0199049 | A1 | 10/2003 | Nguyen |
| 2007/0190620 | A1 | 8/2007 | Mueller |
| 2007/0225383 | A1 | 9/2007 | Cortright |
| 2008/0033188 | A1 | 2/2008 | Dumesic |

OTHER PUBLICATIONS

Campbell et al, The End of Cheap Oil, Scientific American Mar. 1998, pp. 78-84.
Klass, Biomass for renewable energy, fuels and chemical, pp. 10-19, (1998).
Pimentel, Ethanol Fuels: Energy Balance, Economics,and Environmental Impacts are Negative,Natural Resources Research, vol. 12, No. 2, Jun. 2003, pp. 127-137.
Roman-Leshkov et al, Production of dimethylfuran for liquid fuels frombiomass-derived carbohydrates, Nature, Jun. 2007,pp. 982-986.
Zhao et al, Metal Chlorides in Ionic Liquid Solvents Convert Sugars to5-Hydroxymethylfurfural, Science 316, 1597 (2007).
Yong et al, Efficient Catalytic System for the Selective Production of 5-Hydroxymethylfurfural from Glucose and Fructose, Angew. Chem. Int. Ed. 2008, 47, 9345-9348.
Binder et al, Simple Chemical Transformation of Lignocellulosic Biomassinto Furans for Fuels and Chemicals, J. Am. Chem. Soc. 2009, 131, 1979-1985 9 1979.
Huber, et al., Production of Liquid Alkanes by Aqueous-Phase Processing of Biomass-Derived Carbohydrates,Science 308, 1446 (2005).
Mascal et al, Direct, High-Yield Conversion of Cellulose into Biofuel, Angew. Chem. Int. Ed. 2008, 47, 7924-7926.

(Continued)

*Primary Examiner* — Andrew D Kosar
*Assistant Examiner* — Raymond Covington
(74) *Attorney, Agent, or Firm* — Law Offices John A. Parrish

(57) ABSTRACT

The invention relates to a method for manufacture of hydrocarbon fuels and oxygenated hydrocarbon fuels such as alkyl substituted tetrahydrofurans such as 2,5-dimethyltetrahydrofuran, 2-methyltetrahydrofuran and mixtures thereof. The method generally entails forming a mixture of reactants that includes carbonaceous material water, a metal catalyst and an acid reacting that mixture in the presence of hydrogen. The reaction is performed at a temperature and for a time sufficient to produce a furan type hydrocarbon fuel. The process may be adapted to provide continuous manufacture of hydrocarbon fuels such as a furan type fuel.

21 Claims, 1 Drawing Sheet

OTHER PUBLICATIONS

Chundawat et al, Effect of Particle Size Based Separation of Milled Corn Stover on AFEX Pretreatment and Enzymatic Digestibility, Biotechnology and Bioengineering, vol. 96, No. 2, Published online Aug. 10, 2006.

Poster Paper: A Research Roadmap for Making Lignocellulosic Biofuels a Practical Reality, Jun. 2007.

Kunkes, et al., Catalytic Conversion of Biomass to Monofunctional Hydrocarbons and Targeted Liquid-Fuel Classes, Science 322, 417 (2008).

Ragauskas, et al., The Path Forward for Biofuels and Biomaterials, Science 311, 484 (2006).

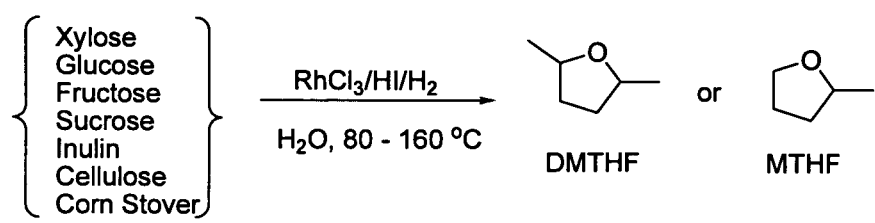

ONE-STEP CATALYTIC CONVERSION OF BIOMASS-DERIVED CARBOHYDRATES TO LIQUID FUELS

This application claims priority to U.S. Provisional Patent Application 60/129,160 filed Jun. 6, 2008.

FIELD OF THE INVENTION

The invention generally relates to manufacture of liquid fuels. More particularly, the invention relates to manufacture of liquid fuels from biomass-derived materials such as monosaccharides and polysaccharides.

BACKGROUND OF THE INVENTION

The production of renewable liquid fuels directly from biomass resources is of great importance in view of the present high consumption of fossil fuels. Today, about three quarters of the world's energy is provided by fossil fuels such as coal, oil, and natural gas. Fossil fuels, however, are nonrenewable resources. Diminishing reserves of fossil fuels and growing concerns about global warming call for sustainable sources of energy such as renewable liquid fuels.

A known method for producing liquid fuels from biomass entails fermentation of sugars to produce ethanol. Ethanol, however, is not a good candidate for a liquid fuel due to its low energy density (23 MJ/L), high volatility (BP 78° C.), and high solubility in water (fully miscible). Other liquid fuel candidates such as 2,5-dimethylfuran (DMF) and 2,5-dimethyltetrahydrofuran (DMTHF) which can be produced from renewable biomass therefore have gained interest.

It is known to use a two-step synthesis of 2,5-dimethylfuran (DMF) liquid fuel via 5-hydroxymethylfurfural (HMF) produced by dehydration of fructose. DMF, compared to ethanol, possesses higher energy density (31.5 MJ/L), lower volatility (BP 92-94° C.) and is immiscible with water. However, the application of this two-step synthesis is limited due to low yield and complicated separations. Moreover, a typical method for manufacture of HMF from cellulose entails either aqueous acid hydrolysis at high temperatures and pressures (250-400° C., 10 MPa) at less than 30% yield or using expensive ionic liquid as solvent.

Although methods for manufacture of biomass derived liquid fuels are known, these methods have numerous disadvantages as discussed above.

A need therefore exists for a method of generating renewable liquid fuels that addresses the disadvantages of the prior art.

BRIEF DESCRIPTION OF THE DRAWINGS

FIG. 1 shows single step conversion of various biomass derived carbohydrates and cellulosic biomass into tetrahydrofuran type liquid fuels.

SUMMARY OF THE INVENTION

The invention relates to single step catalytic conversion process for conversion of lignocellulosic biomasses as well as biomass-derived carbohydrates into tetrahydrofuran type compounds for fuels Examples of these fuels include but are not limited to 2,5-dimethyltetrahydrofuran (DMTHF), 2-methyltetrahydrofuran (MTHF) and tetrahydrofuran derivatives such as 2,5 dimethylfuran, 2-ethyltetrahydrofuran, 2-methyltetrahydrofuran, tetrahydro-5-methylfuran-2-methanol, tetrahydro-5-methylfuran-2-carbaldehyde, and 2-methylcyclopentanone.

Conversion may be performed with high yield. Conversion may be performed by use of an acid such as HI optionally with an alkali halide salt such as NaCl, NaI and mixtures thereof, HCl optionally with an alkali halide salt such as NaCl, NaI and mixtures thereof, HBr and $H_2SO_4$ optionally with an alkali halide salt such as NaCl, NaI and mixtures thereof, preferably HI. Conversion is performed in the presence of a metal catalyst such as supported and unsupported Rh, Ru, Pd, Ni, Ir, Cr, Co, and their salts, preferably $RhCl_3 \cdot xH_2O$ under $H_2$ where the $H_2$ is at a pressure of about 30 PSI to about 1000 PSI, preferably about 100 PSI to about 500 PSI, more preferably about 300 PSI, at about 25° C. to about 200° C., preferably about 80° C. to about 160° C., for about 1 h to about 44 h, preferably about 3 h to about 16 h.

Starting materials that may be used in the conversion process include but not limited to hexoses (such as glucose, fructose, mannose, galactose, sorbose, etc.), pentoses (such as xylose, ribose, arabinose, etc.), as well as other mono-, di-, oligo-, and polysaccharides (such as sucrose, cellubiose, amylose, inulin, starch, cellulose, hemi-cellulose, xylan, etc.), and the like. Where xylose is employed in the conversion process, 2-methyltetrahydrofuran (MTHF) liquid fuel is produced with high selectivity. The conversion process may be used to treat a wide variety of biomass feedstock, including raw lignocellulosic biomass such as plant leaves, roots, seeds, and stalks, corn stalks, straw, seed hulls, sugarcane leavings, jatropha, switchgrass, corn stover and nutshells; (2) wood materials such as wood or bark, sawdust, timber slash, and mill scrap; (3) municipal waste such as waste paper and yard clippings; and (4) energy crops such as poplars, willows, switch grass, alfalfa, prairie bluestem, corn, soybean, and the like.

In one aspect, the invention relates to a method for manufacture of hydrocarbon fuels and oxygenated hydrocarbon fuels such as alkyl substituted tetrahydrofurans such as 2,5-dimethyltetrahydrofuran, 2-methyltetrahydrofuran and mixtures thereof. The method entails forming a mixture of reactants that includes a carbonaceous material such as hexoses, pentoses, polysaccharides, lignocelluloses and mixtures thereof, water, a metal catalyst and an acid is reacted in the presence of hydrogen. The reaction may be performed at a temperature of about 25° C. to about 200° C. for a time sufficient to produce a furan type hydrocarbon fuel. The hydrogen may be employed at a pressure of about 30 psi to about 1000 psi. Where the carbonaceous material is a hexose, the hydrogen pressure may be about 200 psi to about 500 psi and the hexose may be any of glucose, fructose, mannose, galactose, sorbose and mixtures thereof, preferably fructose. The metal catalyst may be any one or more of supported Rh, Ru, Pd, Ni, Ir, Cr, Co, unsupported Rh, Ru, Pd, Ni, Ir, Cr, Co, salts of any of Rh, Ru, Pd, Ni, Ir, Cr, Co, mixtures thereof and the acid may be any one or more of HI, HCl, HBr, $H_2SO_4$, and solid acids such as phosphotungstic acid and mixtures thereof. Preferably, the metal catalyst is $RhCl_3 \cdot xH_2O$ and the mixture may further include an organic solvent such as $C_6H_5Cl$.

In another aspect, the invention relates to manufacture of furan derivative fuel from biomass derived carbohydrates. In this aspect, the method entails forming a mixture of reactants that includes a carbonaceous material such as fructose, glucose, inulin, sucrose, cellulose, xylose and mixtures thereof, a metal catalyst, an acid, and an organic solvent. The mixture is reacted under hydrogen at an elevated temperature for a period of about 4 hrs to about 20 hrs to produce a furan derivative fuel.

In yet another aspect, the invention relates to a method of conversion of a lignocellulose to a furan type fuel. In this aspect, the method entails forming a mixture comprising a lignocellulose, metal catalyst, water, acid, and alkali halide salt and aromatic solvent. The mixture is reacted in hydrogen at a pressure of about 30 psi to about 500 psi at a temperature of about 80° C. to about 200° C. to produce a furan fuel and the lignocellulose may be any of plant leaves, roots, seeds, corn stalks, straw, seed hulls, sugarcane leavings, jatropha, switchgrass, corn stover, nutshells, wood, sawdust, poplars, willows, switch grass, alfalfa, prairie bluestem, corn, corn stover and mixtures thereof. Preferably, the lignocellulose is corn stover, the catalyst is $RhCl_3 \cdot xH_2O$, the acid is HCl, the salt is NaI, the solvent is benzene, the hydrogen is at a pressure of about 300 psi and the temperature is about 160° C.

In yet another aspect, the invention relates to a method of continuous manufacture of a furan type fuel. In this aspect, the invention entails forming a reaction mixture of a carbonaceous material, acid, water and metal catalyst, reacting the mixture under hydrogen at elevated temperature for a time sufficient to generate a reaction product comprising a furan type fuel, acid, water and metal catalyst, combining the reaction product with an aromatic solvent to form a solvent blend having the fuel therein, removing the solvent layer having the fuel therein from the reaction product, adding additional amount of carbonaceous material to form a second reaction mixture and repeating this sequence.

Having summarized the invention, the invention is described in further detail below by reference to the following detailed description and non-limiting examples.

DETAILED DESCRIPTION OF THE INVENTION

Materials $RhCl_3 \cdot xH_2O$ (Rh 38.5-45.5%) as well as metal catalysts such as Pd/C, Ru/C, $RuCl_3$, Rh/C, $NiI_3$, $PdI_3$, $RhI_3$, and $IrCl_3 \cdot xH_2O$ that may be employed herein, singly or in combination, are commercially available from sources such as Alfa Aesar.

Glucose, fructose, sucrose, inulin, cellulose and xylose are available from Sigma-Aldrich and Alfa Aesar.

High-pressure hydrogen is available from GT&S, Inc. and used without further purification.

Isotopically enriched chemicals such as $C_6D_6$ and $D_2O$ are obtained from Cambridge Isotope Laboratories and used without further purification.

Feedstock:

Feedstocks for use in the present method can comprise any carbohydrate. Thus, for example, suitable feedstocks include hexoses (such as glucose, fructose, mannose, galactose, sorbose, etc.), pentoses (such as xylose, ribose, arabinose, etc.), as well as other mono-, di-, oligo-, and polysaccharides (such as sucrose, cellubiose, amylose, inulin, starch, cellulose, hemi-cellulose, xylan, etc.), and the like.

As used herein, the term "biomass" refers to the organic materials produced by plants, such as leaves, roots, seeds, and stalks without limitation. Common sources of biomass include (without limitation): (1) agricultural wastes, such as corn stalks, straw, seed hulls, sugarcane leavings and nutshells; (2) wood materials such as wood or bark, sawdust, timber slash, and mill scrap; (3) municipal waste such as waste paper and yard clippings; and (4) energy crops such as poplars, willows, switch grass, alfalfa, prairie bluestem, corn, soybean, and the like.

Catalyst Selection

Metal catalysts for use in the conversion process may be selected on the basis of effective hydrogenation catalysts that are stable under acidic conditions employed. Catalysts that may be employed include but are not limited to supported and unsupported Rh, Ru, Pd, Ni, Ir, Cr, Co, and their salts and mixtures thereof.

Conversion

The conversion process, as shown in FIG. 1, generally entails reacting an aqueous mixture of starting materials that includes a carbonaceous material such as any one or more of hexoses, pentoses, polysaccharides, lignocelluloses and mixtures thereof. Hexoses that may be used include but not limited to glucose, fructose, mannose, galactose, sorbose and mixtures thereof; pentoses that may be used include but not limited to xylose, ribose, arabinose and mixtures thereof; polysaccharides that may be employed include not limited to sucrose, inulin, cellulose, cellobiose, hemi-cellulose, xylan, and mixtures thereof as well as lignocelluloses that may be used include but not limited to corn stover, plant leaves, roots, seeds, corn stalks, straw, seed hulls, sugarcane leavings, jatropha, switchgrass, corn stover, nutshells, wood, sawdust, poplars, willows, switch grass, alfalfa, prairie bluestem, corn, and mixtures thereof, a metal catalyst and an acid. The mixture is reacted under hydrogen at about 80 C to about 160 C for about 2 hr to about 44 hr to yield tetrahydrofuran type fuels such as DMTHF, MTHF. The acids that may be employed include but are not limited to HI optionally with an alkali halide salt such as NaCl, NaI and mixtures thereof, HCl optionally with an alkali halide salt such as NaCl, NaI and mixtures thereof, HBr, $H_2SO_4$ optionally with an alkali halide salt such as NaCl, NaI and mixtures thereof, as well as mixtures of these acids.

In an alternative embodiment, an organic solvent may be added to the mixture prior to reacting the starting materials as described above. Examples of solvents that may be employed include but are not limited to aromatics such as benzene, toluene, chlorobenzene and mixtures thereof as well as alkanes such as isooctane, decane and mixtures thereof, as well as mixtures of aromatics and alkanes. The organic solvents may be added to the mixture in amounts of about 10 wt. % to about 200 wt %, preferably about 50 wt % to about 100 wt % based on the weight of aqueous mixture.

The process is further illustrated below by reference to the following, non-limiting examples.

Single Step Synthesis of Furan Type Fuel Such as DMTHF from Hexoses Such as Fructose Generally, single step synthesis of furan type fuels such as DMTHF from hexoses such as fructose entails forming a mixture of a hexose, water, and acid optionally with an aromatic solvent and metal catalyst. The mixture is reacted at a temperature of about 25° C. to about 200° C., preferably about 50° C. to about 140° C. under hydrogen at a pressure of about 30 psi to about 500 psi, preferably about 300 psi for about 1 hrs to about 16 hrs, preferably about 2 hrs to about 6 hrs.

Examples 1 to 13 show conversion of aqueous mixtures that include fructose (pH of 1.0 to −1.0) with HI acid and $RhCl \cdot xH_2O$ as catalyst under hydrogen atmosphere. The results are shown in Table 1. In examples 1 to 13, the amount of DMTHF is determined by $^1H$ NMR using nitromethane as internal standard.

Example 1

Fructose (1 mmol, 8 wt % in water), HI (9 mmol, 57 wt % in water) and $RhCl_3 \cdot xH_2O$ (0.1 mmol) are added to a glass reaction vial in open air to form a mixture. The vial containing the mixture then is placed into a bomb, flushed with $H_2$, and charged with 300 psi $H_2$. The bomb is placed into an oil bath at 25° C. for a period of 6 h to react the mixture to generate DMTHF liquid fuel. Then, 4 ml benzene is added to extract the liquid fuel. The benzene layer having the liquid fuel is removed and analyzed to assess the amount of DMTHF present in the reaction product.

The reaction product is analyzed by an $^1$H NMR (Bruker Avance-360 spectrometer equipped with a quadnuclear probe that operates at 360.13 MHz), GC (HP Hewlett Packard-5890 series II with a FID detector; 95% dimethyl- and 5% diphenyl-polysiloxane column) and GC-MS (Waters GC-TOF with Agilent 6890 GC; 20 meter 150 µm I.D.; 0.15 µm 95% methyl/5% phenyl silicone film column; 70 eV electron ionization). Product identification is performed by $^1$H NMR and GC-MS. For comparison, DMTHF and MCPO are purchased from Sigma-Aldrich and compared with the $^1$H NMR spectra and the retention time from GC of the reaction product produced.

The method used for GC is as follows: The initial oven temperature is 40° C.; then the temperature is ramped at 3° C./min up to 100° C. and then the temperature is ramped at 10° C./min up to 200° C. and held for 5 min. The method used for GC-MS is as follows: The initial oven temperature is 40° C. and is held for 1 min; the temperature is ramped at 15° C./min up to 290° C. and held for 7 min. The total time elapsed is 25 min. The injector temperature is 290° C. with a split of 20/1. The helium flow rate is 0.5 ml/min. The temperature of the transfer line is 220° C. The Mass scan is 35-650 Da/sec. The identification of products is predicted by GC-MS library and confirmed by $^1$H NMR and the retention time of GC. Retention times of the products in GC using the method described above are: DMTHF: 4.6 min and 4.8 min; $^1$H NMR is used to determine the yield of DMTHF by using nitromethane as internal standard.

Example 2

The procedure of example 1 is employed except that the oil bath has a temperature of 80° C. to enable reaction of the mixture at 80° C.

Example 3

The procedure of example 1 is employed except that the oil bath has a temperature of 100° C. to enable reaction of the mixture at 100° C.

Example 4

The procedure of example 1 is employed except that 4 ml benzene is added to the mixture before the reaction and the oil bath has a temperature of 80° C. to enable reaction of the mixture at 80° C.

Example 5

The procedure of example 1 is employed except that 4 ml benzene and 0.6 g NaCl each are added to the mixture before the reaction and the oil bath has a temperature of 80° C. to enable reaction of the mixture at 80° C.

Example 6

The procedure of example 1 is employed except that 4 ml toluene is added to the mixture before the reaction and the oil bath has a temperature of 80° C. to enable reaction of the mixture at 80° C.

Example 7

The procedure of example 1 is employed except that (1 mmol, 6 wt % fructose in water), 1.5 mmol HI and 4 ml toluene each are added to the mixture and the oil bath has a temperature of 120° C. for 4 hr to enable reaction of the mixture at 120° C.

Example 8

The procedure of example 1 is employed except that (1 mmol, 6 wt % fructose in water), 1.2 mmol HI and 4 ml chlorobenzene each are added to the mixture, and the bomb containing the mixture is maintained for 2.5 hrs in an oil bath that has a temperature of 140° C. to enable reaction of the mixture at 140° C.

Example 9

The procedure of example 1 is employed except that (1 mmol, 6 wt % fructose in water), 1.2 mmol HCl is substituted for HI, and 4 ml benzene is added to the mixture and the bomb containing the mixture is maintained for 2 hr in an oil bath at temperature of 140° C. to enable reaction of the mixture at 140° C. for 2 hr.

Example 10

The procedure of example 1 is employed except that (1 mmol, 6 wt % fructose in water), 1.2 mmol HBr is substituted for HI, and 4 ml benzene each are added to the mixture and the bomb having the mixture is placed into an oil bath at a temperature of 140° C. for 3 hr to enable reaction of the mixture at 140° C.

Example 11

The procedure of example 1 is employed except that (1 mmol, 6 wt % fructose in water), 0.6 mmol $H_2SO_4$ is substituted for HI, and 4 ml benzene is added to the mixture and the bomb having the mixture is placed into an oil bath at a temperature of 140° C. for 2 hr to enable reaction of the mixture at 140° C.

Example 12

The procedure of example 1 is employed except that (1 mmol, 10 wt % fructose in water), 0.05 mmol $RhCl_3.xH_2O$, 1.2 mmol HI and 4 ml chlorobenzene each are added to the mixture and the bomb having the mixture is placed into an oil bath at a temperature of 140° C. for 3 hr to enable reaction of the mixture at 140° C.

Example 13

The procedure of example 1 is employed except that (1 mmol, 20 wt % fructose in water), 0.01 mmol $RhCl_3.xH_2O$, 1.2 mmol HI, and 4 ml chlorobenzene each are added to the mixture and the bomb having the mixture is placed into an oil bath at a temperature of 140° C. for 3 h to enable reaction of the mixture at 140° C.

TABLE 1

Synthesis of DMTHF from Fructose in One Step

| EX. | RhCl$_3$·xH$_2$O | Temp. | Acid | Extractant | Time | Yield of DMTHF |
|---|---|---|---|---|---|---|
| 1 | 0.1 (mmol) | 25(° C.) | HI 9(mmol) | — | 6(h) | 0(%) |
| 2 | 0.1 | 80 | HI 9 | — | 6 | 51 |
| 3 | 0.1 | 100 | HI 9 | — | 6 | 39 |
| 4 | 0.1 | 80 | HI 9, | Benzene | 6 | 81 |
| 5 | 0.1 | 80 | HI 9, | Benzene, NaCl | 6 | 72 |
| 6 | 0.1 | 80 | HI 9, | Toluene | 6 | 78 |
| 7 | 0.1 | 120 | HI 1.5, | Toluene | 4 | 83 |
| 8 | 0.1 | 140 | HI 1.2, | C$_6$H$_5$Cl | 2.5 | 85 |
| 9 | 0.1 | 140 | HCl 1.2, | Benzene, | 2 | 5 |
| 10 | 0.1 | 140 | HBr 1.2, | Benzene | 3 | 2 |
| 11 | 0.1 | 140 | H$_2$SO$_4$ 0.6, | Benzene | 2 | 0 |
| 12 | 0.05 | 140 | HI 1.2, | C$_6$H$_5$Cl | 3 | 79 |
| 13 | 0.01 | 140 | HI 1.2, | C$_6$H$_5$Cl | 3 | 67 |

Separation of Fuel Products and Recycling of Catalyst.

In the disclosed process, DMTHF may be separated from the aqueous reaction phase by use of organic solvent extractants such as aromatic solvents such as benzene, toluene, chlorobenzene and mixtures thereof, alkane solvents such as isooctane, decane and mixtures thereof, as well as mixtures of aromatic solvents and alkane solvents. However, where the organic solvent also may be used as a liquid fuel, DMTHF need not be separated from organic solvent. Examples of solvents that may be used as liquid fuels include but are not limited to isooctane, decane and DMTHF.

Advantageously, the RhCl$_3$.xH$_2$O catalyst employed in the acidic aqueous reaction mixtures in the disclosed process remains active after separation of liquid fuel reaction products. The process therefore may be performed as a continuous process where additional carbohydrates may be continuously added and the process repeated. This is illustrated by use of repetition of the reaction process of example 4 for ten cycles.

After each reaction cycle, and upon removal of the benzene extraction layer, an additional 1 mmol fructose and 4 ml benzene are added to the aqueous reaction mixture for use in a subsequent reaction cycle. Results of repeated cycling are shown in Table 2. Yield of DMTHF is determined by $^1$H NMR using nitromethane as internal standard. Table 2 shows that a reaction system that includes HI acid and RhCl$_3$.xH$_2$O catalyst remains active through at least 10 cycles without little or no reduction in yield.

TABLE 2

Recycling of Catalyst in Fructose Conversion

| Cycle | 1 | 2 | 3 | 4 | 5 | 6 | 7 | 8 | 9 | 10[a] |
|---|---|---|---|---|---|---|---|---|---|---|
| DMTHF yield (%) | 81 | 91 | 85 | 82 | 85 | 79 | 91 | 86 | 83 | 84 |

[a]The aqueous reaction mixture is filtered and the filtrate used for cycle 10. The $^1$H-NMR spectrum of the benzene layer from cycle 3, Table 2 shows that cis and trans DMTHF isomers are present in a 9:1 ratio.

Single Step Synthesis of Furan Type Fuel Such as DMTHF from Glucose.

Generally, single step synthesis of furan type fuels such as DMTHF from hexoses such as glucose entails forming a mixture of a hexose, water, acid, metal catalyst and aromatic solvent such as chlorobenzene. The mixture is reacted at a temperature of about 50° C. to about 200° C., preferably about 80° C. to about 160° C., under hydrogen at a pressure of about 30 psi to about 500 psi, preferably about 300 psi for about 4 hrs to about 20 hrs, preferably about 16 hrs.

Examples 14 to 19 show conversion of glucose in aqueous solution (pH of 1.0 to −1.0) with HI acid and RhCl$_3$.xH$_2$O as catalyst. The results are shown in Table 3.

Example 14

Glucose (1 mmol, 6 wt % in water), HI (9 mmol, 57 wt % in water), RhCl$_3$.xH$_2$O (0.1 mmol), 4 ml chlorobenzene are added to a glass reaction vial in open air to form a mixture. Then the vial is placed into a bomb, flushed with H$_2$, and charged with 300 psi H$_2$. The bomb is placed into an oil bath at 80° C. for 16 h to react the mixture to generate DMTHF. The chlorobenzene layer that contains DMTHF is analyzed as described above.

Example 15

The procedure of example 14 is employed except that 1.9 mmol HI is used and the oil bath has a temperature of 120° C.

Example 16

The procedure of example 14 is employed except that 1.5 mmol HI is used and the oil bath has a temperature of 140° C.

Example 17

The procedure of example 14 is employed except that 1.2 mmol HI is used and the oil bath has a temperature of 160° C.

Example 18

The procedure of example 14 is employed except that 1.5 mmol HI is used and the oil bath has a temperature of 140° C. for 4 hours.

Example 19

The procedure of example 14 is employed except that 1.5 mmol HI is used and the oil bath has a temperature of 140° C. for 8 hours.

TABLE 3

Synthesis of DMTHF from Glucose in One Step

| Ex. | Temp (° C.) | HI (mmol) | Time (h) | DMTHF yield (%) |
|---|---|---|---|---|
| 14 | 80 | 9 | 16 | 4 |
| 15 | 120 | 1.9 | 16 | 64 |

TABLE 3-continued

Synthesis of DMTHF from Glucose in One Step

| Ex. | Temp (° C.) | HI (mmol) | Time (h) | DMTHF yield (%) |
|---|---|---|---|---|
| 16 | 140 | 1.5 | 16 | 74 |
| 17 | 160 | 1.2 | 16 | 71 |
| 18 | 140 | 1.5 | 4 | 46 |
| 19 | 140 | 1.5 | 8 | 58 |

Single Step Synthesis of Furan Derivative Fuel from Biomass Derived Carbohydrates.

Generally, single step synthesis of furan derivative type fuels such as DMTHF from hexoses such as fructose entails forming a mixture of a hexose, water, acid and metal catalyst and aromatic solvent such as chlorobenzene. The mixture is reacted at a temperature of about 80° C. to about 160° C., preferably about 140° C., under hydrogen at a pressure of about 30 psi to about 500 psi, preferably about 300 psi, for about 4 hrs to about 20 hrs, preferably about 16 hrs.

Examples 20 to 25 illustrate Synthesis of Furan Derivatives as liquid fuels from biomass derived carbohydrates. The results are shown in Table 4.

Example 20

Fructose (1 mmol, 6 wt % in water), HI (1.5 mmol, 57 wt % in water), $RhCl_3 \cdot xH_2O$ (0.1 mmol), 4 ml chlorobenzene are added to a glass reaction vial in open air to form a mixture. Then the vial is put into a bomb, flushed with $H_2$, and charged with 300 psi $H_2$. The bomb is placed into an oil bath at 140° C. for 16 h to react the mixture and to generate a reaction product that includes the furan derivatives. The resulting chlorobenzene layer that includes the furan derivative is analyzed as described above. GC-MS analysis of the organic layer shows that DMTHF is the major product and that small amounts of other C6 reaction side products. These C6 side products include 2,5-dimethylfuran, 2-ethyltetrahydrofuran, 2-methyltetrahydropyran, and tetrahydro-5-methylfuran-2-methanol (For xylose, only MTHF is formed as the only product). The C6 side products also may be extracted using procedure employed to extract fuels such as DMTHF for use as liquid fuels.

Example 21

The procedure of example 20 is employed except that glucose (1 mmol, 6 wt % in water) is substituted for fructose.

Example 22

The procedure of as example 20 is employed except that inulin (1 mmol, 6 wt % in water) is substituted for fructose.

Example 23

The procedure of example 20 is employed except that Sucrose (1 mmol, 6 wt % in water) is substituted for fructose.

Example 24

The procedure of example 20 is employed except that cellulose (1 mmol, 6 wt % in water) is substituted for fructose.

Example 25

The procedure of example 20 is employed except that xylose (1 mmol, 6 wt % in water) is substituted for fructose.

TABLE 4

Transformation of Carbohydrates to Liquid Fuels

| Ex. | | DMTHF | MTHF | 2,5-dimethyl-furan | 2-ethyltetra-hydrofuran | 2-methyltetra-hydropyran | tetrahydro-5-methylfuran-2-methanol | Total Chemical Yield[a] | Conversion[b] |
|---|---|---|---|---|---|---|---|---|---|
| 20 | Fructose | 85% | 0 | 0(%) | 5(%) | 1(%) | 1(%) | 92(%) | 100(%) |
| 21 | Glucose | 74 | 0 | 1 | 5 | 3 | 0 | 83 | 100 |
| 22 | Inulin | 77 | 0 | 0 | 5 | 0 | 1 | 83 | 96 |
| 23 | Sucrose | 86 | 0 | 0 | 4 | 0 | 0 | 90 | 96 |
| 24 | Cellulose | 57 | 0 | 4 | 6 | 1 | 0 | 68 | 90 |
| 25 | Xylose | | 80% | 0 | 0 | 0 | 0 | 80 | 95 |

Yield is determined by $^1H$ NMR and GC analysis using nitromethane as internal standard.
[a]Sum of DMTHF and C6 reaction side products.
[b]Conversion based on the leftover glucose in aqueous layer using DMSO as internal standard.

Single Step Synthesis of Furan Type Fuel Such as DMTHF from Cellulose.

Generally, single step synthesis of furan type fuels such as DMTHF from cellulose entails forming a mixture of cellulose, water, and acid preferably with an alkali halide salt, an aromatic solvent and metal catalyst. The mixture is reacted at a temperature of about 80° C. to about 200° C., preferably about 160° C. about 170° C. under hydrogen at a pressure of about 30 psi to about 500 psi, preferably about 300 psi for about 4 hrs to about 20 hrs, preferably about 16 hrs.

Examples 27 to 33 illustrate Single Step Synthesis of DMTHF from Cellulose. Example 26 is a comparative example that illustrates yield of DMTHF from conversion of glucose. The results are shown in Table 5.

Example 26

Glucose (0.18 g, 1 mmol), $RhCl_3 \cdot xH_2O$ (15 mg, 0.07 mmol), water (1.8 ml), HCl (50 µl, 0.57 mmol), NaI (300 mg, 2 mmol), benzene (4 ml) are added to a glass reaction vial in open air to form a mixture. Then the vial is placed into a bomb, flushed with $H_2$, and charged with 300 psi $H_2$. The bomb then is placed into an oil bath and heated to 160° C. for 16 h to react the mixture. The resulting benzene layer that includes DMTHF is removed for analysis.

Example 27

The procedure of example 26 is employed except that Cellulose (0.18 g) is substituted for glucose.

Example 28

The procedure of example 26 is employed except that Cellulose (0.18 g) is substituted for glucose and 70 µl HCl (0.8 mmol) is used and the reaction lasts for 18 h.

Example 29

The procedure of example 26 is employed except that Cellulose (0.18 g) is substituted for glucose and 300 mg NaI (2 mmol) is used and the reaction lasts for 18 h.

Example 30

The procedure of example 26 is employed except that Cellulose (0.18 g) is substituted for glucose, 70 µl HCl (0.8 mmol), and 300 mg NaI (2 mmol) are used.

Example 31

The procedure of example 26 is employed except that Cellulose (0.18 g) is substituted for glucose, 70 µl HCl (0.8 mmol), and 300 mg NaI (2 mmol) are used and the reaction is performed at 170° C. for 18 h.

Example 32

The procedure of example 26 is employed except that Cellulose (0.18 g) is substituted for glucose, 70 µl HCl (0.8 mmol), and 300 mg NaI (2 mmol) are used and the reaction is performed for 3 h.

Example 33

The procedure of example 26 is employed except that Cellulose (0.18 g) is substituted for glucose, 70 µl HCl (0.8 mmol), and 300 mg NaI (2 mmol) are used and the reaction is performed for 6 h.

TABLE 5

Single Step Synthesis of DMTHF from Cellulose

| Ex. | Biomass | HCl (µl) | NaI (mg) | Temp (° C.) | Time (h) | DMTHF Yield (%)[a] |
|---|---|---|---|---|---|---|
| 26 | glucose | 50 | 200 | 160 | 16 | 80 |
| 27 | cellulose | 50 | 200 | 160 | 16 | 0 |
| 28 | cellulose | 70 | 200 | 160 | 18 | 57 |
| 29 | cellulose | 50 | 300 | 160 | 18 | 79 |
| 30 | cellulose | 70 | 300 | 160 | 16 | 80 |
| 31 | cellulose | 70 | 300 | 170 | 18 | 68 |
| 32 | cellulose | 70 | 300 | 160 | 3 | 45 |
| 33 | cellulose | 70 | 300 | 160 | 6 | 70 |

[a]Yield of DMTHF is determined by $^1$H NMR using nitromethane as internal standard.

Single Step Production of Furan Type Fuels from Cellulose and Lignocellulosic Biomass.

Generally, single step synthesis of furan type fuels such as DMTHF from lignocellulosic biomass entails forming a mixture of a biomass, water, and acid preferably with an alkali halide salt, an aromatic solvent, and metal catalyst. The mixture is reacted at a temperature of about 80° C. to about 200° C., preferably about 160° C. under hydrogen at a pressure of about 30 psi to about 500 psi, preferably about 300 psi for about 4 hrs to about 20 hrs, preferably about 16 hrs.

Examples 34 to 35 illustrate Single Step Synthesis of MTHF from cellulose and Lignocellulosic Biomass. The results are shown in Table 6.

Example 34

Cellulose (0.18 g), $RhCl_3 \cdot xH_2O$ (15 mg, 0.07 mmol), water (1.8 ml), HCl (70 µl, 0.8 mmol), NaI (300 mg, 2 mmol), benzene (4 ml) are added to a glass reaction vial in open air to form a mixture. Then the vial is placed into a bomb, flushed with $H_2$, and charged with 300 psi $H_2$. The bomb then is placed into an oil bath and heated to 160° C. for 16 h to react the mixture. The resulting benzene layer is removed for analysis.

Example 35

The procedure of example 34 is employed except that corn stover (0.18 g) is substituted for cellulose.

TABLE 6

Results from cellulose and untreated corn stover

| Ex. | Biomass | DMTHF | 2,5-dimethyl-furan | 2-ethyltetra-hydrofuran | Tetrahydro-5-methylfuran-2-methanol | 2-methylcyclo-pentanone | MTHF | Conversion |
|---|---|---|---|---|---|---|---|---|
| 34 | cellulose | 80 | — | 5 | 2 | — | — | 100 |
| 35 | Corn Stover[a] | 49 | 11 | — | — | 3 | 56 | 100 |

[a]Except for MTHF, yields of DMTHF and other side products are based on glucan present in corn stover (37.4 wt %). Yield of MTHF is based on xylan present in corn stover (21.1 wt %).

In another aspect, solid acids such as phosphotungstic acid may be employed. This is illustrated in examples 36-38.

In this aspect, a hexose, cellulose or combination thereof is mixed with an acid, an alkali halide salt, water, metal catalyst and aromatic solvent to form a mixture. The mixture is reacted under hydrogen at a pressure of about 30 psi to about 500 psi, preferably about 300 psi at a temperature of about 80° C. to about 200° C., preferably about 140° C. to about 160° C. in the presence of an aromatic solvent for about 4 hrs to about 20 hrs, preferably about 6 hrs to about 16 hrs.

Example 36

Fructose (1 mmol, 10 wt % in water), $RhCl_3$ (0.1 mmol), $H_3PW_{12}O_{40}$ (0.3 mmol), NaI (2 mmol), $H_2$ (300 psi), benzene (4 ml) are reacted at 140° C. for 16 h. The yield of 72% DMTHF in the benzene layer is determined by $^1$H NMR using nitromethane as internal standard.

Example 37

Glucose (1 mmol, 10 wt % in water), $RhCl_3$ (0.1 mmol), $H_3PW_{12}O_{40}$ (0.3 mmol), NaI (2 mmol), $H_2$ (300 psi), benzene (4 ml) are reacted at 140° C. for 16. The yield of 51% DMTHF in the benzene layer is isolated yield determined by $^1$H NMR using nitromethane as internal standard.

Example 38

Cellulose (1 mmol, 10 wt % in water), $RhCl_3$ (0.1 mmol), $H_3PW_{12}O_{40}$ (0.3 mmol), NaI (2 mmol), $H_2$ (300 psi), benzene (4 ml) are reacted at 160° C. for 16 h. The yield of 47% DMTHF in the benzene layer is determined by $^1$H NMR using nitromethane as internal standard.

Conversion of Di- and Polysaccharides Directly into Furan Type Fuel

In another aspect, di- and polysaccharides are directly converted into fuel such as furan type liquid fuel, as illustrated by examples 39-41. The conversion generally entails reacting a mixture of a polysaccharide such as cellobiose, an acid, water, metal catalyst, aromatic solvent under hydrogen at a pressure of about 30 psi to about 500 psi, preferably about 300 psi at a temperature of about 80° C. to about 200° C., preferably about 140° C. in the presence of an aromatic solvent for about 4 hrs to about 20 hrs, preferably about 16 hrs.

Example 39

Cellubiose (1 mmol, 6 wt % in water), HI (1.5 mmol, 57 wt % in water), RhCl$_3$.xH$_2$O (0.1 mmol), 4 ml benzene are added to a glass reaction vial in open air to form a mixture. Then the vial is put into a bomb, flushed with H$_2$, and charged with 300 psi H$_2$. The bomb is placed into an oil bath at 140° C. for 16 h. The resulting benzene layer that includes DMTHF liquid fuel is analyzed as described above. The yield of DMTHF was determined by 1HNMR using nitromethane as internal standard, which is 62%.

Example 40

The procedure of example 39 is followed except that 1 mmol of amylose is substituted for cellobiose. The yield of DMTHF is determined to be 42%.

Example 41

The procedure of example 39 is followed except that 1 mmol of starch is substituted for amylose. The yield of DMTHF is determined to be 18%.

The invention claimed is:

1. A method for manufacture of hydrocarbon fuels and oxygenated hydrocarbon fuels comprising,
reacting a mixture of reactants comprising a carbonaceous material selected from the group consisting of hexoses, pentoses, polysaccharides, lignocelluloses and mixtures thereof, water, a metal catalyst and an acid in the presence of hydrogen at a temperature of about 25° C. to about 200° C. for a time sufficient to produce a furan type hydrocarbon fuel in the absence of further processing steps wherein the metal catalyst is Rh, the acid is HI and the pressure of hydrogen is about 30 psi to about 1000 psi.

2. The method of claim 1 wherein the carbonaceous material is a hexose and the pressure is about 200 psi to about 500 psi.

3. The method of claim 2 wherein the hexose is selected from the group consisting of glucose, fructose, mannose, galactose, sorbose and mixtures thereof.

4. The method of claim 3 wherein the hexose is fructose.

5. The method of claim 1 wherein the fuel is an alkyl substituted tetrahydrofuran.

6. The method of claim 5 wherein the alkyl substituted tetrahydrofuran is selected from the group consisting of 2,5-dimethyltetrahydrofuran, 2-methyltetrahydrofuran and mixtures thereof.

7. The method of claim 6 wherein the metal catalyst is RhCl$_3$.xH$_2$O, the acid is HI and the pressure of Hydrogen is about 300 psi.

8. The method of claim 1 wherein the mixture further comprises an organic solvent.

9. The method of claim 7 wherein the mixture further comprises C$_6$H$_5$Cl.

10. The method of claim 1 wherein the carbonaceous material is glucose and the acid is HI.

11. A method for manufacture of furan derivative liquid fuel from biomass derived carbohydrate comprising,
forming a mixture of reactants comprising a carbonaceous material selected from the group consisting of fructose, glucose, inulin, sucrose, cellulose, xylose and mixtures thereof, a metal catalyst, an acid, and an organic solvent, and
reacting the mixture under hydrogen at an elevated temperature for a period of about 4 hrs to about 20 hrs to produce a furan derivative fuel.

12. The method of claim 11 wherein the carbonaceous material is glucose.

13. The method of claim 11 wherein carbonaceous material is cellulose.

14. The method of claim 13 wherein the acid is HI and the solvent is chlorobenzene.

15. A method of conversion of a lignocellulose to a furan type fuel comprising,
forming a mixture comprising a lignocellulose, metal catalyst, water, acid, alkali halide salt and aromatic solvent,
reacting the mixture in hydrogen at a pressure of about 30 to about 500 psi at a temperature of about 80° C. to about 200° C. to produce a furan fuel.

16. The method of claim 15 wherein the lignocellulose is selected from the group consisting of plant leaves, roots, seeds, corn stalks, straw, seed hulls, sugarcane leavings, jatropha, switchgrass, corn stover, nutshells, wood, sawdust, poplars, willows, switch grass, alfalfa, prairie bluestem, corn, corn stover and mixtures thereof.

17. The method of claim 16 wherein the lignocellulose is corn stover.

18. The method of claim 16 wherein the lignocellulose is cellulose.

19. The method of claim 16 wherein the catalyst is RhCl$_3$xH20, the acid is HCl, the salt is NaI and the solvent is benzene.

20. The method of claim 19 wherein the hydrogen is at a pressure of about 300 psi and the temperature is about 160° C.

21. A method of continuous manufacture of a furan type fuel comprising,
step a. forming a reaction mixture of a carbonaceous material, acid, water and metal catalyst,
step b. reacting the mixture under hydrogen at elevated temperature for a time sufficient to generate a reaction product comprising a furan type fuel, acid, water and metal catalyst
step c. combining the reaction product with an aromatic solvent to form a solvent blend having the fuel therein,
step d. removing the solvent layer having the fuel therein from the reaction product,
step e. adding additional amount of carbonaceous material to form a second reaction mixture and
repeating steps a to e.

* * * * *